(12) United States Patent
Somberg

(10) Patent No.: US 11,364,213 B2
(45) Date of Patent: Jun. 21, 2022

(54) METHOD OF INITIATING OR ESCALATING DOFETILIDE DOSE AND FORMULATIONS THEREFOR

(71) Applicant: Academic Pharmaceuticals, Inc., Lake Bluff, IL (US)

(72) Inventor: John Somberg, Lake Bluff, IL (US)

(73) Assignee: Academic Pharmaceuticals Inc, Lake Bluff, IL (US)

( * ) Notice: Subject to any disclaimer, the term of this patent is extended or adjusted under 35 U.S.C. 154(b) by 317 days.

(21) Appl. No.: 16/449,796

(22) Filed: Jun. 24, 2019

(65) Prior Publication Data

US 2019/0388371 A1 Dec. 26, 2019

Related U.S. Application Data

(60) Provisional application No. 62/689,442, filed on Jun. 25, 2018.

(51) Int. Cl.
| | | |
|---|---|---|
| *A61K 31/18* | (2006.01) | |
| *A61K 47/02* | (2006.01) | |
| *A61K 47/10* | (2017.01) | |
| *A61K 47/18* | (2017.01) | |
| *A61K 47/26* | (2006.01) | |
| *A61K 9/00* | (2006.01) | |
| *A61K 47/12* | (2006.01) | |

(52) U.S. Cl.
CPC ............ *A61K 31/18* (2013.01); *A61K 9/0019* (2013.01); *A61K 9/0053* (2013.01); *A61K 47/02* (2013.01); *A61K 47/10* (2013.01); *A61K 47/12* (2013.01); *A61K 47/18* (2013.01); *A61K 47/26* (2013.01)

(58) Field of Classification Search
CPC .... A61K 31/18; A61K 9/0019; A61K 9/0053; A61K 47/02; A61K 47/10; A61K 47/12; A61K 47/18; A61K 47/26
USPC ......................................................... 514/600
See application file for complete search history.

(56) References Cited

U.S. PATENT DOCUMENTS 9,597,302 B1 * 3/2017 Yan ...................... A61K 9/0053

OTHER PUBLICATIONS

Zelewski Cleveland Clinic Pharmacotherapy Update, 2000, 3(4) pp. 1-3 (Year: 2000).*
Coz et al Clinical Pharmacology and Therapeutics, 1995, 57(5), 533-542 (Year: 1995).*
Wada et al (Clin Pharmacokinet, 1998, 35(1), 1-7 (Year: 1998).*
NDA 020931/S-003, FDA Supplemental Approval Letter, signed Jul. 11, 2011, 7 pages.
NDA 20-931 Tikosyn (dofetilide), Risk Evaluation and Mitigation Strategy Document, Jul. 11, 2011, 69 pages.

\* cited by examiner

*Primary Examiner* — Yevgeny Valenrod
(74) *Attorney, Agent, or Firm* — Vance Intellectual Property, PC

(57) ABSTRACT

The present invention provides a novel method of initiating or escalating dofetliide dosage with the goal of maximizing patient safety while shortening the time period required for electrocardiographic monitoring from three days to one day.

20 Claims, No Drawings

METHOD OF INITIATING OR ESCALATING DOFETILIDE DOSE AND FORMULATIONS THEREFOR

FIELD OF THE INVENTION

The present invention provides a novel method of initiating or escalating dofetliide dosage with the goal of maximizing patient safety while shortening the time period required for electrocardiographic monitoring from three days to one day.

BACKGROUND OF THE INVENTION

Dofetilide (β-((p-methanesulfonamidophenethyl)methylamino)methanesulfono-p-phenetidide) is an anti-arrhythmic of the Vaughn Williams Class III. Its action is to prolong the action potential duration, specifically by prolonging repolarization time. Dofetilide does this by blocking the outward potassium channel IKr (rapid potassium rectifier current). This action is both anti-arrhythmic and pro-arrhythmic. Excessive prolongation of the repolarization time may give rise to life threatening arrhythmias, especially those called Torsade de Pointe ventricular tachycardia (Tpd). The repolarization time of cardiac cells may be manifest on the body surface ECG (electrocardiogram) by an increase in the QT interval. Since the QT interval varies with heart rate, often the QT interval is measured as the heart rate corrected QT, called the QTc. Prolongation of the QTc interval by pharmaceutical agents may give rise to arrhythmia. Thus, in the initial loading phase, or in a dose escalation procedure, it is critical to monitor the QTc interval to avoid excessive QTc prolongation and thus the possible development of life threatening ventricular tachycardias, especially those of the Tdp variety. For these reasons FDA has mandated in hospital QTc monitoring in initial dofetilide loading or for dose escalation.

Telemetry monitoring is both expensive and time consuming for patients, physicians, and health care professionals. Because it takes at least 3 days for dofetilide to reach a steady state concentration and thus for the concentration to be reflected in full expression in QTc prolongation. Patients may leave the hospital early endangering themselves to possible arrhythmias occurring outside the hospital where help is often not available. For reasons of safety, cost, and convenience, it would be useful to obtain initial dose loading or dose escalation, achieving serum dofetilide concentrations that reach the maximal peak levels seen with daily dosing in the shortest period, thus reducing the time needed for in hospital monitoring.

The relationship between blood concentration of dofetilide and QTc can be expressed as: QTc=baseline QTc+(slope relationship×blood dofetilide concentration). The relationship between dofetilide plasma concentration and QTc has been previously established. The QTc changes between 15-25 msec/ng/mL (average=20 msec) as reported by Sedgwick et al, Br J. Clin Pharmacol 1991:31:515-519. Thus, for a patient with an initial QTc of 405 msec QT who received a dose IV of 2.4 µg/kg that would be analogous to a chronic dose of 500 µg bid would be expected to show a QTc of 459 msec on average, a 13% increase over baseline, within acceptable limits.

$$QTc=405 \text{ msec}+(20 \text{ msec/ng/mL} \times 2.7 \text{ ng/mL})=459 \text{ msec}$$

When administering dofetilide, a physician first assesses the QTc interval. If the QTc is greater than 440 msec (500 msec in patients with ventricular conduction abnormalities), dofetilide is not indicated. The physician then calculates the patient's creatinine clearance employing the following formulas:

Creatinine clearance (male)=[(140−Age)×Body Wt (kg)]/[72×serum creatinine (mg/dL)]

Creatinine clearance (female)=Creatine clearance (male)×0.85

Following calculation of creatinine clearance, the starting dose of dofetilide is determined as:

| Creatinine Clearance | Starting Dose of Dofetilide |
| --- | --- |
| 60 mL/min | 500 µg bid |
| 40-60 mL/min | 250 µg bid |
| 20-40 mL/min | 125 µg bid |
| <20 mL/min | Dofetilide not indicated |

The physician then must monitor the QTc till steady state is achieved, in this case 5-6 doses, or 3 days in hospital with ECG monitoring. This is a costly, time intensive procedure.

If Cmax ss, the maximal concentration obtained at steady state, can be achieved in less than 24 hrs., the maximum QTc will be obtained in the 24 hr. period and thus risk assessed in one day or less reducing cost, increasing compliance, as well as enhancing patient safety.

Thus, it would be beneficial to discover formulations of dofetilide that would allow for one-day loading and methods of one-day dofetilide loading.

SUMMARY OF THE INVENTION

Accordingly, in an aspect, the present invention provides a novel method of one-day loading of dofetilide in a patient in need thereof.

In another aspect, the present invention provides novel pharmaceutical compositions, comprising: a therapeutically effective amount of dofetilide and a pharmaceutically acceptable carrier, wherein the pharmaceutical is suitable for intravenous administration.

These and other objects, which will become apparent during the following detailed description, have been achieved by the inventors' discovery that dofetilide can be titrated in one day.

DETAILED DESCRIPTION OF THE INVENTION

All references cited herein are hereby incorporated in their entirety herein by reference.

One day loading with dofetilide is possible with the use of IV (intravenous) dofetilide in combination with oral dosing, obviating the delays seen with GI absorption and distribution. IV dofetilide kinetics are linear permitting a direct relationship between IV dose of dofetilide administered and serum concentration obtained. With IV administration one can avoid "overshoot" in serum concentration, avoiding excessive dofetilide blood levels and thus possible arrhythmias. The relationship between serum concentration and QTc interval is well known, with a high degree of correlation.

Administering an IV infusion of dofetilide would achieve serum dofetilide concentration equivalent to that reached as steady state (Cmax ss) in one day under ECG observation. Prior studies have reported that a single dose of dofetilide, following a 10 min. infusion of 1.5 µg/kg yielded a peak plasma concentration of 1.74 ng/mL. Sedgwick et al. An infusion of 3.0 µg/mL resulted in a plasma concentration of 5.35 ng/mL (Sedquick et al, B J. Clin Pharmacol 1991:31: 515-519 and Rasmussen et al J. Cardiolvascular Pharmacology 20:1992, S96-101). Coz and associates (Clin Pharmacology & Therapeutics, 1995; 57(5) 533-54) reported that a 500 µg oral dose of dofetilide yielded a plasma concentration Cmax of 1.9 ng/mL. Thus, if a single dose reaches 70% of predicted steady state, at steady state, one can estimate Cmax ss to be 2.7 ng/mL, if 500 µg/mL was administered twice daily for at least 5 doses. If an IV dose of 1.5 µg/kg is known to result in a peak level of 1.7 ng/mL, a dose of 2.4 µg/kg, assuming linear kinetics, would reach a peak concentration of 2.7 ng/mL, exposing the patient to the peak serum concentration predicted for steady state and thus the maximum QTc prolongation. This would fully expose the patient to the potentially greatest arrhythmic risk in a short period of time, while monitored in hospital.

The initial loading of a 500 µg dose could be achieved by IV administration (e.g., by using one of the IV formulations described in as depicted in Examples 2-4).

Thus, in an aspect, the present invention provides a novel method to initiate dofetilide IV in patients with a medical indication to receive chronic oral dofetilide therapy.

In another aspect, the present invention provides for the use of an IV infusion to obtain dofetilide predicted Cmax commensurate to the level of exposure that would occur with chronic oral dosing.

In another aspect, the present invention provides a novel method of dofetilide administration using an IV loading dose that would be reflected in ECG changes; specifically, prolongation in the QTc that would permit dose adjustments to avoid excessive QTc prolongation.

In another aspect, the present invention provides a novel method of decreasing chronic oral dosing of dofetilide based on QTc increments, thereby avoiding excessive QTc prolongation.

In another aspect, the present invention provides a novel method of dofetilide loading in 24 hrs or less to obtain plasma dofetilide concentration predicted to be maximal at steady state from a single IV loading regimen.

In another aspect, the present invention provides a novel method of dose adjustment of chronic oral dofetilide therapy based on initial creatinine clearance (calculated) that permits dose adjustments (down titration) based on QTc observed following initial dofetilide loading.

In another aspect, the present invention provides a novel method of rapidly titrating and chronically administering dofetilide, comprising:
 a. infusing intravenously, to a patient in need thereof, dofetilide in an amount that achieves the predicted maximal serum concentration from 500 µg dofetilide orally administered;
 b. measuring the QTc of the patient;
 c. after completion of the intravenous administration, orally administering a first 500 µg dose of dofetilide;
 d. chronically administering 500 µg dofetilide orally, twice daily;
 provided that if the patient's QTc has increased by 15% over baseline QTc or if the QTc greater than 500 msec (550 msec seen in patients with ventricular conduction abnormalities), the chronic oral dosages of dofetilide are reduced to 250 µg.

In another aspect, the patient has a calculated GFR (glomerular filtration rate) of greater than 60 mL/min.

In another aspect, the patient presents with intermittent AF (atrial fibrillation).

In another aspect, the patient is monitored via electrocardiography.

In another aspect, dofetilide is infused at 1.8-3.0 µg/kg. Additional examples of the amount of dofetilide infused include: (a) 1.8, 1.9, 2.0, 2.1, 2.2, 2.3, 2.4, 2.5, 2.6, 2.7, 2.8, 2.9, and 3.0 µg/kg, (b) 2.0-2.8 µg/kg, (c) 2.2-2.6 µg/kg, (d) 2.3 µg/kg, (e) 2.4 µg/kg, and (f) 2.5 µg/kg.

In another aspect, dofetilide is infused over a period of 10 minutes. Additional examples of the infusion time period include 5, 6, 7, 8, 9, 10, 11, 12, 13, 14, 15, 16, 17, 18, 19, 20, 21, 22, 23, 24, 25, 26, 27, 28, 29, and 30 minutes.

In another aspect, the patient's QTc is measured at baseline (prior to dofetilide administration) and then measured periodically thereafter (e.g., every thirty minutes in a hospital setting or when visiting a physician or medical office). In another aspect, the patients QTc is measured every 30 minutes until the dofetilide dosage is titrated. The QTc can then be measured periodically thereafter. The QTc can be measured at other intervals if more (shorter time period) or less data (longer time periods) data is desired.

In another aspect, if the patient has a calculated GFR (glomerular filtration rate) of between 40-60 mL/min, the first oral dosage of dofetilide and chronic dosages are 250 µg. In another aspect, the chronic dosage is reduced to 125 µg due to a QTc that increased by 15% over baseline QTc or a QTc greater than 500 msec is observed (550 msec seen in patients with ventricular conduction abnormalities).

In another aspect, if the patient has a calculated GFR (glomerular filtration rate) of between 20-40 mL/min, the first oral dosage of dofetilide and chronic dosages are 125 µg. In another aspect, the treatment is discontinued if the patient's QTc is increased by 15% over baseline QTc or a QTc greater than 500 msec is observed (550 msec seen in patients with ventricular conduction abnormalities).

Chronic dosing or chronically administering refers to administration of dofetilide beyond the hospital setting (e.g., daily administration until the patient is advised otherwise). The length of administration includes days (e.g., 2, 3, 4, 5, or 6), weeks (e.g., 1, 2, 3, 4, 5, 6, 7, or 8), months (e.g., 1, 2, 3, 4, 5, 6, 7, 8, 9, 10, 11, or 12), years (e.g., 1, 2, 3, 4, or 5), or for the lifetime of the patient.

In another aspect, the present invention provides a novel pharmaceutical composition, comprising:
 a. 10-1000 µg/mL Dofetilide;
 b. 1-20% by volume 1,3-propanediol; and
 c. water;
 wherein the composition is suitable for intravenous administration.

Further examples of the concentration of Dofetilide include: (a) 10, 20, 30, 40, 50, 60, 70, 80 90, 100, 110, 120, 130, 140, 150, 160, 170, 180, 190, 200, 220, 240, 260, 280, 300, 320, 340, 360, 380, 400, 420, 440, 460, 480, and 500 µg/mL, (b) 10-500 µg/mL, (c) 10-100 µg/mL, (d) 20-80 µg/mL, (e) 30-70 µg/mL, (f) 40-60 µg/mL, and (g) 50 µg/mL.

Further examples of the concentration of 1,3-propanediol include: (a) 1, 2, 3, 4, 5, 6, 7, 8, 9, 10, 11, 12, 13, 14, 15, 16, 17, 18, 19, and 20% by volume, (b) 2-10% by volume, (c) 3-8% by volume, (d) 4-6% by volume, and (e) 5% by volume.

Examples of the pH of the 1,3-propanediol intravenous formulation include 4, 5, 6, and 7.

In another aspect, the present invention provides a novel pharmaceutical composition, comprising:
a. 10-1000 µg/mL Dofetilide;
b. 0.005-0.015 M HCl;
c. 0.05-0.15 M acetic acid;
d. 0.05-0.15 M sodium acetate; and
e. water;
wherein the composition is suitable for intravenous administration.

Further examples of the concentration of Dofetilide include: (a) 10, 20, 30, 40, 50, 60, 70, 80 90, 100, 110, 120, 130, 140, 150, 160, 170, 180, 190, 200, 220, 240, 260, 280, 300, 320, 340, 360, 380, 400, 420, 440, 460, 480, and 500 µg/mL, (b) 10-500 µg/mL, (c) 10-100 µg/mL, (d) 20-80 µg/mL, (e) 30-70 µg/mL, (f) 40-60 µg/mL, and (g) 50 µg/mL.

Further examples of the concentration of HCl include: (a) 0.005, 0.006, 0.007, 0.008 0.009, 0.010, 0.011, 0.012, 0.013, 0.014, and 0.015M, (b) 0.007-0.013M, (c) 0.008-0.012 M, and (d) 0.01M.

Further examples of the concentration of acetic acid include: (a) 0.05, 0.06, 0.07, 0.08 0.09, 0.10, 0.11, 0.12, 0.13, 0.14, and 0.15M, (b) 0.07-0.013M, (c) 0.08-0.1 M, (d) 0.09M, and (e) 0.1M.

Further examples of the concentration of sodium acetate include: (a) 0.05, 0.06, 0.07, 0.08 0.09, 0.10, 0.11, 0.12, 0.13, 0.14, and 0.15M, (b) 0.07-0.013M, (c) 0.08-0.1 M, (d) 0.09M, and (e) 0.1M.

Examples of the pH of the HCl intravenous formulation include 4, 5, 6, and 7.

In another aspect, the present invention provides a novel pharmaceutical composition, comprising:
a. 10-1000 µg/mL Dofetilide;
b. 0.1-5% by volume N,N-Dimethylacetamide; and,
c. 1-50% D-glucose in water;
wherein the composition is suitable for intravenous administration.

Further examples of the concentration of Dofetilide include: (a) 10, 20, 30, 40, 50, 60, 70, 80 90, 100, 110, 120, 130, 140, 150, 160, 170, 180, 190, 200, 220, 240, 260, 280, 300, 320, 340, 360, 380, 400, 420, 440, 460, 480, and 500 µg/mL, (b) 10-500 µg/mL, (c) 10-100 µg/mL, (d) 20-80 µg/mL, (e) 30-70 µg/mL, (f) 40-60 µg/mL, and (g) 50 µg/mL.

Further examples of the concentration of N,N-Dimethylacetamide include: (a) 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.2, 2.4, 2.6, 2.8, 3, 3.2, 3.4, 3.6, 3.8, 4, 4.2, 4.4, 4.6, 4.8, and 5% by volume, (b) 0.2 to 4% by volume, (c) 0.5-2% by volume, (d) 0.8% by volume, (e) 0.9% by volume, (f) 1% by volume, and (g) 1.1% by volume.

Further examples of the concentration of D-Glucose in water include: (a) 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, and 50%, (b) 1-25%, (c) 1-10%, (d) 2-7%, (e) 3%, (f) 4%, (g) 5%, (h) 6%, nd (i) 7%.

Examples of the pH of the D-glucose intravenous formulation include 6, 7, 8 and 9.

The present invention may be embodied in other specific forms without departing from the spirit or essential attributes thereof. This invention encompasses all combinations of aspects of the invention noted herein. It is understood that any and all embodiments of the present invention may be taken in conjunction with any other embodiment or embodiments to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

Other features of the invention will become apparent in the course of the following descriptions of exemplary embodiments that are given for illustration of the invention and are not intended to be limiting thereof.

EXAMPLES

Example 1

A 70 kg patient with a calculated GFR (glomerular filtration rate) of greater than 60 mL/min presents with intermittent atrial fibrillation (AF) and the physician decides to treat the patient with dofetilide. The patient would be admitted to hospital, ECG continuously monitored, and an IV infusion of dofetilide administered at 2.4 µg/kg that is expected to achieve the predicted maximal serum concentration that one would expect from 500 µg dofetilide orally. This would reach peak, if administered orally, after 6 doses twice daily of dofetilide. The peak concentration will typically be reached at termination of infusion (typically a 10-minute infusion). QTc would be measured every 30 mins. A maintenance dose (500 µg dofetilide orally) would be administered approximately one hour after start of the IV infusion. After the infusion and oral dose of dofetilide, the peak concentration will be reached in 4 h and then at 8 h a trough concentration will be reached, and a second oral dose can be administered.

If the QTc has increased by 15% over baseline QTc, or if a QTc greater than 500 msec is observed (550 msec seen in patients with ventricular conduction abnormalities) subsequent oral doses would be reduced to 250 µg b.i.d.

If patients present with a lower than normal GFR, the initial target concentration would be the same, but the maintenance dose administered would be lower; 250 µg or 125 µg b.i.d (based on the chart below).

| Creatinine Clearance | Starting Oral Dose of Dofetilide |
| --- | --- |
| 60 mL/min | 500 µg bid |
| 40-60 mL/min | 250 µg bid |
| 20-40 mL/min | 125 µg bid |
| <20 mL/min | Dofetilide not indicated |

In patients that show excessive QTc prolongation at initial loading (greater than 500 msec (550 msec seen in patients with ventricular conduction abnormalities)), the first oral dose would be reduced to 250 µg (or 125 µg if starting oral dose was 250 µg based on the above chart) and the peak concentration expected in 4 h with QTc re-evaluated. In this way, a concentration projection from a dofetilide chronic oral dosing of 250 µg could be readily evaluated, with QTc observation and the patient could still be discharged in ~24 hrs. This would permit the measurement of the QTc response at the highest QTc concentration projected that the patient would be exposed to chronically.

Example 2

Dofetilide IV Formulation (50 µg/mL):
a. 2 mg of Dofetilide powder was weighed out.
b. 1 mL of 1,3-propanediol was added.
c. The solution was vortexed for 1 minute and then sonicated for 5-10 min.

d. 1.0 mL of 1,3-propanediol was added and the resulting solution vortexed again to completely dissolve all powder (5% 1,3-propanediol by final volume).
e. The resulting solution was diluted with water (~38 mL) to achieve a final concentration of 50 µg/mL.
f. The final formulation had a pH=5.0.
g. The formulation was stable for 3 months RT (no turbidity or precipitate observed).

Example 3

Dofetilide IV Formulation (50 µg/mL):
a. 2 mg of Dofetilide powder was weighed out.
b. 4 mL of 0.1 M HCl was added (0.01 M HCl in final formulation).
c. The solution was vortexed for 5 minutes until all the powder dissolved.
d. 36 mL of 0.1 M acetic acid and 0.1 M sodium acetate in water was added (0.09 M acetic acid and sodium acetate in final formulation).
e. The resulting solution was shaken for 5 seconds.
f. The final formulation had a pH=4.46.
g. The solution was stable for 3 months RT (no turbidity or precipitate observed).

Example 4

Dofetilide IV Formulation (50 µg/mL):
a. 5 mg of Dofetilide powder was weighed out.
b. 1 mL of N,N-Dimethylacetamide was added (1% by volume).
c. The mixture was shaken for 5 seconds.
d. 99 mL of 5% D-glucose in water was added (~5% D-glucose in final formulation).
e. The solution was shaken for 5 seconds.
f. The final formulation had a pH=7.25
g. The solution was stable for 3 months RT (no turbidity or precipitate observed).

Comparative Examples A-K

Procedure:
a. Final Volume: 10 mL.
b. Final Concentration of Dofetilide: 50 µg/mL (1 mg of Dofetlilide).
c. Temperature: warmed to 25° C. to encourage dissolution.
d. Solubilization: all samples showed turbidity and/or precipitation within 3 months.

The following eleven (11) formulations were made and tested and shown to be unsuitable as an intravenous Dofetilide formulation.

| Ex. # | Solvent/Solvating Agent | pH | Vortex | Sonicate | Warmed | Solubilized |
|---|---|---|---|---|---|---|
| A | Lactic acid (tested 1, 5, and 10% by weight) | 4.5-6.5 | Y | Y | Y | N |
| B | Tween 80 (tested 1, 5, and 10% by weight) | 5-7.8 | Y | Y | Y | N |
| C | Triton X 100 (tested 1, 5, and 10% by weight) | 5-7.8 | Y | Y | Y | N |
| D | DMSO (tested 1, 5, and 10% by volume) | 5-7.8 | Y | Y | Y | N |
| E | Ethanol (tested 1, 5, 10, and 20% by volume) | 5-7.8 | Y | Y | Y | N |
| F | Ethanol (tested 1, 5, 10, and 20% by volume) + HP-β-CD (tested 1, 5, 10, and 15% by weight) | 5-7.8 | Y | Y | Y | N |
| G | Ethanol (tested 1, 5, 10, and 20% by volume) + DMSO (tested 1, 5, and 10% by volume) | 5-7.8 | Y | Y | Y | N |
| H | PEG 40 (tested 1, 5, 10, and 20% by weight) | 5-7.8 | Y | Y | Y | N |
| I | Olive oil (tested 1, 5, 10, and 20% by volume) | 5-7.8 | Y | Y | Y | N |
| J | MCT oil (tested 1, 5, and 10% by volume) | 5-7.5 | Y | Y | Y | N |
| K | 1,2-Propanediol (tested 1, 5, and 10% by volume)/ Tween 80 (tested 1, 5, 10, and 20% by weight) | 5-7.5 | Y | Y | Y | N |

Tween 80: Polyoxyethylene (80) sorbitan monolaurate (80 repeating units of ethylene glycol).

Triton X 100: Polyethylene glycol p-(1,1,3,3-tetramethylbutyl)-phenyl ether (t-Oct-$C_6H_4$—$(OCH_2CH_2)_xOH$, x = 9-10)

DMSO: dimethylsulfoxide.

HP-β-CD: hydroxy-propyl-β-cyclodextrin.

PEG 40: polyethylene glycol 40.

MCT oil: medium-chain triglyceride oil.

Numerous modifications and variations of the present invention are possible in light of the above teachings. It is therefore to be understood that within the scope of the appended claims, the invention may be practiced otherwise that as specifically described herein.

What is claimed is:

1. A method of rapidly titrating and chronically administering dofetilide, comprising:
   a. infusing intravenously dofetilide to a patient in need of chronic dofetilide therapy, wherein the amount and duration of dofetilide infused is sufficient to reach a serum concentration equivalent to a predicted maximal serum steady state concentration of orally administered dofetilide for the patient;
   b. measuring the QTc of the patient;
   c. after completion of the intravenous administration, orally administering a first dosage of dofetilide that is based on the renal function of the patient, provided that the first oral dosage is given less than 8 hours after initiation of the intravenous infusion;
   d. chronically administering every 12 hours a further oral dosage of dofetilide that is based on the renal function of the patient;
   provided that if the patient's QTc has increased by 15% over baseline QTc or if the QTc is greater than 500 msec or 550 msec in patients with ventricular conduction abnormalities, the oral dosages of dofetilide are reduced;
   wherein the predicted maximal serum steady state concentration is based on the renal function of the patient;
   wherein the intravenous and first two oral dosages are such that three steady state maximum serum concentrations of dofetilide are achieved in less than 24 hours from the initiation of the intravenous infusion.

2. The method of claim 1, wherein the patient has a calculated GFR (glomerular filtration rate) of greater than 60 mL/min and the first oral dosage of dofetilide and further chronic oral dosages are 500 µg.

3. The method of claim 1, wherein the patient presents with intermittent AF (atrial fibrillation).

4. The method of claim 1, wherein the patient is monitored via electrocardiography.

5. The method of claim 1, wherein dofetilide is infused at 3 µg/kg.

6. The method of claim 1, wherein dofetilide is infused over a period of 30 minutes.

7. The method of claim 1, wherein the patients QTc is measured every 30 minutes until the dofetilide dosage is titrated.

8. The method of claim 1, wherein if the patient has a calculated GFR (glomerular filtration rate) of between 40-60 mL/min, the first oral dosage of dofetilide and further chronic oral dosages are 250 µg.

9. The method of claim 8, wherein the further chronic oral dosage is reduced to 125 µg due to a QTc that increased by 15% over baseline QTc or a QTc greater than 500 msec or 550 msec in patients with ventricular conduction abnormalities is observed.

10. The method of claim 1, wherein if the patient has a calculated GFR (glomerular filtration rate) of between 20-40 mL/min, the first oral dosage of dofetilide and further chronic oral dosages are 125 µg.

11. The method of claim 10, wherein the treatment is discontinued if the patient's QTc is increased by 15% over baseline QTc or a QTc greater than 500 msec or 550 msec in patients with ventricular conduction abnormalities is observed.

12. The method of claim 1, wherein the patient has a calculated GFR of greater than 60 mL/min and the patient presents with intermittent AF.

13. The method of claim 1, wherein dofetilide is infused at 3 µg/kg over a period of 30 minutes.

14. The method of claim 13, wherein the patients QTc is measured every 30 minutes until the dofetilide dosage is titrated.

15. The method of claim 13, wherein the patient has a calculated GFR of greater than 60 mL/min.

16. The method of claim 13, wherein the patient presents with intermittent AF (atrial fibrillation).

17. The method of claim 13, wherein if the patient has a calculated GFR of between 40-60 mL/min, the first oral dosage of dofetilide and further chronic oral dosages are 250 µg and the chronic dosage is reduced to 125 µg due to a QTc that increased by 15% over baseline QTc or a QTc greater than 500 msec or 550 msec in patients with ventricular conduction abnormalities is observed.

18. The method of claim 13, wherein if the patient has a calculated GFR of between 20-40 mL/min, the first oral dosage of dofetilide and further chronic oral dosages are 125 µg and the treatment is discontinued if the patient's QTc is increased by 15% over baseline QTc or a QTc greater than 500 msec or 550 msec in patients with ventricular conduction abnormalities is observed.

19. The method of claim 1, wherein if the patient has a calculated GFR of between 40-60 mL/min, the first oral dosage of dofetilide and further chronic oral dosages are 250 µg and the chronic dosage is reduced to 125 µg due to a QTc that increased by 15% over baseline QTc or a QTc greater than 500 msec or 550 msec in patients with ventricular conduction abnormalities is observed.

20. The method of claim 1, wherein if the patient has a calculated GFR of between 20-40 mL/min, the first oral dosage of dofetilide and further chronic oral dosages are 125 µg and the treatment is discontinued if the patient's QTc is increased by 15% over baseline QTc or a QTc greater than 500 msec or 550 msec in patients with ventricular conduction abnormalities is observed.

* * * * *